United States Patent [19]

Salmond

[11] 3,976,636

[45] Aug. 24, 1976

[54] PROCESS AND COMPOUNDS

[75] Inventor: William G. Salmond, Kalamazoo, Mich.

[73] Assignee: The Upjohn Company, Kalamazoo, Mich.

[22] Filed: Oct. 10, 1974

[21] Appl. No.: 513,760

[52] U.S. Cl. ............... 260/239.55 R; 260/397.2; 260/606.5 F
[51] Int. Cl.² ............................................ C07J 71/00
[58] Field of Search ............... 260/397.2, 239.55 R; /Machine Searched Steroids

[56] References Cited
UNITED STATES PATENTS 3,822,254  7/1974  Patridge, Jr. et al. ...... 260/239.55 R

*Primary Examiner*—Elbert L. Roberts
*Attorney, Agent, or Firm*—Martin B. Barnacik; Roman Saliwanchik

[57] ABSTRACT

A method for preparing 25-hydroxycholesterol and novel intermediates.

17 Claims, No Drawings

PROCESS AND COMPOUNDS

BRIEF SUMMARY OF THE INVENTION

A method of preparing intermediates and novel intermediates to hydroxylated vitamin $D_2$ and $D_3$ has been discovered. The method comprises a. reacting an aryl Wittig reagent with

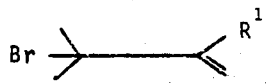

Figure I

, wherein $R^1$ is hydrogen or methyl, to form the phosphonium salt

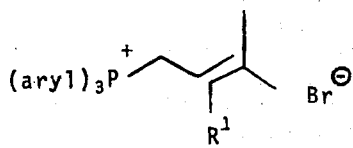

Figure II b. converting the phosphonium salt to the ylide

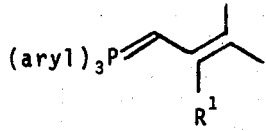

Figure III c. condensing the ylide of Step b with $3\alpha,5\alpha$-cyclo-$6\beta$-alkoxy-bisnorcholanaldehyde wherein alkoxy has from one to six carbon atoms, inclusive, to form the compound

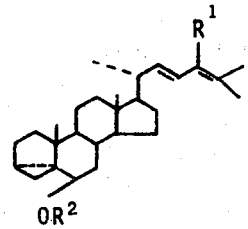

Figure IV wherein $R^1$ is hydrogen or methyl and $R^2$ is alkyl of one to six carbon atoms, inclusive, d. selectively epoxidizing the compound formed in Step c with peralkanoic acid, said alkyl of one to four carbon atoms, inclusive, or peraroic acid, said aryl of six to 10 carbon atoms, inclusive, to form the compounds

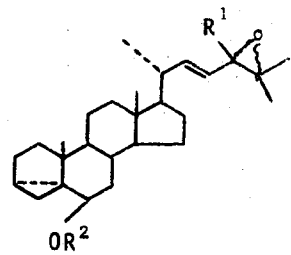

Figure V $R^1$ and $R^2$ as defined above, e. selectively catalytically hydrogenating the unsaturated epoxide formed in Step d with a noble metal catalyst to $3\alpha,5\alpha$-cyclo-$6\beta$-alkoxy 25-hydroxycholesterol derivatives

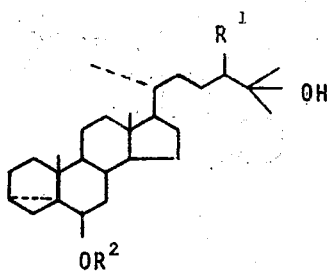

wherein $R^1$ and $R^2$ are defined as above, f. and reversing the $i$-ether formed in Step e to 3-acyloxy-25-hydroxycholesterol derivatives, where acyloxy is two to six carbon atoms, inclusive, by the addition of alkanoic acid, said alkyl having from one to five carbon atoms, inclusive.

Another aspect of the invention is the formation of a phosphonium bromide salt by reacting an aryl Wittig reagent with 3-bromo-3-methylbutene-1 or 3-bromo-2,3-dimethylbutene-1.

A further aspect of the invention is the condensation of $3\alpha,5\alpha$-cyclo-$6\beta$-alkoxybisnorcholanaldehyde with 3-bromo-3-methylbutene-1 or 3-bromo-2,3-dimethylbutene-1 in an alkane solvent having from five to eight carbon atoms, inclusive.

A still further aspect of the invention is the selective epoxidation of the diene of Step c with a peracid selected from the group consisting of a peralkanoic acid, said alkyl group having one to four carbon atoms, inclusive, and a peraroic acid, said aryl groups having from six to 10 carbon atoms, inclusive, to form the $\Delta^{22E}$ olefin epoxide.

Another aspect of the invention is the reversal of $3\alpha,5\alpha$-cyclo-$6\beta$-alkoxy-25-hydroxycholesterol, said alkoxy of one to six carbon atoms, inclusive, to the 3-acyloxy-25-hydroxycholesterol, acyloxy of two to six carbon atoms, inclusive, in an alkanoic acid said alkyl group of the alkanoic acid having one to five carbon atoms, inclusive, said reaction medium essentially free of a mineral or Lewis acid catalyzer.

Another aspect of the invention is the conversion of the $3\alpha,5\alpha$-cyclo-$6\beta$-alkoxy-25-bisnorcholanaldehyde to the $3\alpha,5\alpha$-cyclo-$6\beta$-alkoxy-25-hydroxycholesterol by the (1) condensation of the ylide,

wherein $R^1$ is hydrogen or methyl, with $3\alpha,5\alpha$-cyclo-$6\beta$-alkoxybisnorcholanaldehyde wherein alkoxy is from one to six carbon atoms, inclusive, (2) selective epoxidation of the steroid diene to the $\Delta^{22E}$ epoxide with a peralkanoic or peraroic acid, said alkyl group having one to four carbon atoms and said aryl group having from six to ten carbon atoms, (3) catalytic hydrogenation with a noble metal catalyst to the 25-hydroxycholesterol or 24-methyl derivative.

Further aspects of the invention are the compounds

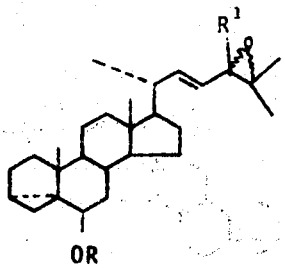

wherein R is alkyl of one to six carbon atoms, inclusive and $R^1$ is hydrogen or methyl and the compounds

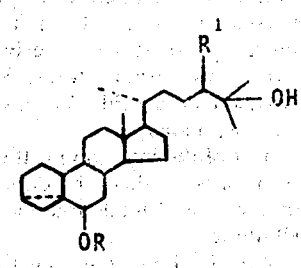

wherein R is alkyl of one to six carbon atoms, inclusive and $R^1$ is hydrogen or methyl.

The 25-hydroxy cholesterols prepared by this invention can be readily converted by known methods to 25-hydroxy Vitamin $D_3$ or derivatives.

DETAILED DESCRIPTION OF THE INVENTION

The term "alkyl" as used throughout the specification and claims include isomerized as well as normal alkyl groups. For example, "alkyl of one to six carbon atoms, inclusive" includes methyl, ethyl, propyl, butyl, pentyl, hexyl, isopropyl, tert. butyl, neopentyl, and 2,3-dimethylbutyl, for instance. The term "aroic" refers to a carboxy acid attached to a substituted or unsubstituted phenyl ring. Examples of such acids include benzoic acid, m-toluic acid, 2,4-dimethylbenzoic acid, m-chlorobenzoic acid, 2,4-diethylbenzoic acid and o-chlorotoluic acid.

The brominated butene used as the starting material for the ylide condensation is prepared by hydrobromination of the appropriate butene under standard conditions. Once prepared, the 3-brominated butene is reacted with a triaryl phosphine to form the phosphonium bromide of the butene. This reaction should be undertaken as soon as possible after the bromination of the butene since the product of that reaction is relatively unstable. The aryl phosphine employed can be triphenyl phosphine or an alkyl substituted phenylphosphine, alkyl of one to four carbon atoms, inclusive, for example, tritolylphosphine or trixylylphosphine. Substituents on the phenyl group can be any functional group which does not interfere with the reaction forming the phosphonium salt, the ylide or the condensation of the ylide with the cholanaldehyde. An example of such a substituent is carboxy forming a compound such as diphenyl, p-carboxyphenyl phosphonium derivative.

Any solvent system which essentially dissolves the reactants and which is inert with respect to the reaction can be employed. Examples of such solvents include halogenated hydrocarbons of one to four carbon atoms, inclusive, for instance, methylene chloride, dichlorethane, chloroform, and dichlorobutane. Care should be taken that the phosphonium salt remains soluble in the solvent system rather than precipitating prematurely as occurs in diethyl ether.

The temperature at which the reaction occurs can be anywhere from about 10°C. to about 50°C. Higher temperatures can be employed, however, decomposition of the bromobutene is a competing reaction which can lower the yield. Preferred temperatures are about 20°C. to about 30°C.

The phosphine is advantageously reacted with the tertiary bromo butene instead of the primary bromo butene. If the latter compound is used, it must be distilled. The distillation is accompanied by significant yield loss through polymerization and decomposition. This loss is minimized by using the tertiary bromobutene with the reaction apparently proceeding through an allylic displacement.

If not already precipitated the phosphonium bromide salt can be precipitated from the solution by the addition of an alkane of five to eight carbon atoms such as pentane or n-hexane. The ylide is then conveniently prepared from the salt by standard procedures such as contacting the salt with an organolithium compound such as n-butyllithium in an alkane solvent such as n-hexane at room temperature.

The $3\alpha,5\alpha$-cyclo-$6\beta$-alkoxy-bisnorcholanaldehyde, alkoxy of one to six carbon atoms, inclusive, is then added to the ylide prepared above for condensation. A solvent system which allows for mutual solubility of the reactants and which is inert to the reactants at the conditions employed can be used. Such solvents as alkanes of five to eight carbon atoms, inclusive, aryl of six to nine carbon atoms, inclusive, and ethers of four to eight carbon atoms, inclusive, can be used. Examples of such solvents include n-pentane, n-hexane, tetrahydrofuran, toluene, and diethylether. The temperature at which the condensation is carried out is not critical and can be from about −20° to about +50°C., preferably from about 10° to about 30°C. A preferred solvent system is the solvent in which the ylide can be suspended and the aldehyde is in solution, for example, an alkane of five to eight carbon atoms, inclusive. When the aldehyde, dissolved in the same alkane, is added to such a suspension of the ylide, a selective formation of the steroid diene occurs. The $\Delta^{22E}$ isomer predominates. This selectivity simplifies the chemical work-up procedure, including separation of the triarylphosphine from the reaction mass. When using tetrahydrofuran as the solvent, the $\Delta^{22E}$ isomer does not predominate. The preferred solvent is n-hexane.

The steroid diene is selectively epoxidized to the $\Delta^{22E}$ olefin. Although the stereochemistry of this compound at $C_{24}$ has not been determined, NMR data suggests that one isomer is present in significantly greater quantities than the other. The agent used to epoxidize the steroid diene is a peralkanoic acid or peraroic acid. The acid employed should be of insufficient strength to react with the steroid nucleus. Peralkanoic acids with alkyl groups of one to four carbon atoms, inclusive, can be conveniently employed. However, substituted peralkanoic acids such as trifluoroperacetic acid should be avoided because of competing reactions with the steroid. When peracetic acid is employed, a buffered solution is generally used because the industrial method of preparing peracetic acid leaves a trace of sulfuric acid. An appropriate buffering vehicle is a sodium carbonate-sodium acetate buffer. Peraroic acids of six to ten carbon atoms can be employed with facility. Such peracids as benzoic, toluic, and xylic are included within this classification. These acids may be substituted with functional groups such as halo forming, for example, m-chloroperbenzoic acid. Peracetic acid is preferred.

The reaction should be carried out in an inert organic solvent in which the reactants are soluble. Solvents such as halogenated hydrocarbons can be used. Examples of such solvents include methylene chloride, chloroform and dichloroethane.

The temperature at which the reaction is carried out is not critical, however, temperatures significantly above room temperature are not preferred because of the lability of the epoxy-olefin product. Temperatures of about −20° to about 40°C. can be employed with −10° to 30°C. preferred.

The epoxy olefin product is now converted to the saturated 25-hydroxylated material by catalytic hydrogenation. The catalyst employed is a noble metal catalyst, for example, platinum and palladium, preferably platinum, which is inert with respect to the hydrogenation conditions employed. The pressure at which the hydrogenation proceeds can vary substantially but should be generally below that pressure which opens the cyclopropane ring of the steroid nucleus since yield is reduced. Pressures ranging from about 5 to about 100 psi can be conveniently employed. Pressures from about 10 to about 50 psi are preferred.

An organic solvent inert to the hydrogenation conditions can be employed. Examples of such solvents are lower alkyl esters of one to six carbon atoms, and halogenated lower alkanes of one to six carbon atoms. Preferred are the halogenated lower alkanes. Illustrative examples of such solvents are ethyl acetate, methyl butyrate, dichloroethane and methylene chloride. A preferred solvent is methylene chloride.

The 25 hydroxylated 3α,5α-cyclo-6β-alkoxy molecule is now reversed to the 3-acyloxy-25-hydroxycholesterol molecule wherein acyloxy is from two to six carbon atoms, inclusive, by the addition of a lower alkanoic acid, said alkyl group having from one to five carbon atoms, inclusive. Acetic acid is preferred. There need not be present catalytic quantities of a strong mineral acid or a Lewis acid for the reaction to take place. The acyl group of the product is the same as the acyl group of the alkanoic acid. The length of reaction time depends upon the reaction temperature. Temperatures ranging from 20°C. to the reflux temperature of the reaction system can be employed.

Following are specific examples illustrative now the scope of the invention. These examples are intended to exemplify and not restrict the scope of this invention. All $R_f$ values are obtained using silica gel.

EXAMPLE 1

3-Methyl-2-butenyltriphenylphosphonium Bromide

Isoprene (60 ml.) is dissolved in 200 ml. methylene chloride and cooled to −10°C. with a methanol/ice bath. HBr gas (40 g.) is then added to the stirred solution during twenty minutes at such a rate to maintain the temperature below +5°C. An exotherm is quite noticeable. After the addition is completed, the mixture is stirred for one hour at room temperature. Triphenylphosphine (131 g.), dissolved in 200 ml. methylene chloride, is then added dropwise at room temperature. After the first 50 ml. of solution has been added, the temperature reaches 34°C. and the excess isoprene begins to boil. The mixture is cooled to 20°C. and the remainder of the triphenylphosphine solution added. The total addition time is 30 minutes. The mixture is then stirred at room temperature for a further 1.5 hours and then Skellysolve B (600 ml.) is added dropwise during 1 hour. A voluminous white crystalline precipitate forms. This is filtered off and dried at room temperature. NMR indicates that this initial product is a solvate containing ½ mole of methylene chloride. The methylene chloride is removed at 65°C. in vacuo. Product m.p. 238°–240°.

EXAMPLE 2

3α,5α-cyclo-6β-methoxycholesta-22t,24-diene

To a slurry of 5.0 g. of the phosphonium salt prepared in Example 1, in 60 ml. hexane, at room temperature and under nitrogen, is added during ca. 2 minutes 7.9 ml. of a 1.6N solution of n-butyl lithium in hexane. A 4°C. exotherm is noted. During this addition the white slurry rapidly gives way to a brick red suspension in a deep red solution, and this mixture is stirred for 40 minutes. After completion of the addition a solution of 3.65 g. of the aldehyde in 20 ml. hexane is added dropwise during 15 minutes. This rate of addition maintains the temperature at between 25°–30°C.

TLC, 10% ethyl acetate in Skellysolve B, shows the reaction to be complete at the end of the addition.[1] During the period of reaction, the dark precipitate gives way to a voluminous lightly colored suspension of triphenylphosphine oxide. The mixture is cooled to 0°C., filtered and the solids washed with 80 ml. of hexane. The combined filtrate is washed three times with 100 ml. portions of water, filtered through sodium sulfate and evaporated in vacuo at 40° to an oil. This is dissolved directly in 50 ml. methylene chloride.

[1] $R_f$ of aldehyde: 0.25; $R_f$ of diene: 0.47

EXAMPLE 3

3α,5α-Cyclo-6β-methoxycholest-22t-en-24,25-oxide

To a stirred solution of the residual oil from Example 2 in 50 ml. of methylene chloride solution is added 3.14 g. powdered anhydrous sodium carbonate followed by 1.5 ml. of the peracetic acid solution which is 43.3% w/v and 2% w/v with respect to sodium acetate. After 40 minutes at room temperature, TLC, 10% ethyl acetate in Skellysolve B, shows presence of starting material so a further 0.5 ml. peracid is added. This is followed 30 minutes later by a further 1.3 g. sodium carbonate and 0.3 ml. peracid. After 25 minutes the mixture is filtered and the solids washed with 50 ml. methylene chloride. The organic phase is washed twice with 50 ml. 10% aqueous sodium sulfite, once with 50 ml. 5% sodium bicarbonate, and three times with 50 ml. water. After filtration through sodium sulfate, the organic solution is evaporated in vacuo at 40°C. to yield an oil.

NMR δ 0.3–0.64 m; 0.75 s (3H); 1.03 s (3H); 1.05 d, J=6 Hz (3H); 1.27 s (3H); 1.33 s (3H); 2.77 m (1H); 3.12 d, J=7 Hz (1H); 3.32 s (3H); 5.33 octet split AB system (2H). R$_f$: 10% AcOEt/Skellysolve B - 0.2; 20% AcOEt/Skellysolve B - 0.53

EXAMPLE 4

3α,5α-Cyclo-6β-methoxy-cholestan-25-ol

After pre-reduction of platinum dioxide (0.37g) in 40 ml. ethyl acetate under 15 psi of hydrogen (approximately 15 minutes), the epoxide prepared in Example 3, dissolved in 60 ml. ethyl acetate, is added and the reduction continued at 15 psi for 1 hour and 40 minutes. At this stage no further uptake of hydrogen has been observed for at least 20 minutes. The reaction mixture is filtered through a bed of celite, a diatomaceous earth, and the solids washed thoroughly with ethyl acetate. The filtrates are evaporated in vacuo and the oily residue dissolved in 10 ml. methylene chloride. To this solution is immediately added 20 ml. acetonitrile. Crystallization begins at once and after 1 hour at 0°C. the mixture is filtered and the crystalline residue collected.

NMR: δ 0.3–0.63 m; 0.73 s (3H); 1.03 s (3H); 1.23 s (6H); 1.78 m (1H); 3.33 s (3H). m.p. 149°-150° ex methylene chloride/acetonitrile R$_f$: 20% AcOEt/Skellysolve B - 0.25

EXAMPLE 5

25-Hydroxycholesteryl Acetate

The i-ether prepared in Example 4 and acetic acid are heated at 70°C. for three hours and the solution poured into water. The mixture is extracted with 100 ml. ethyl acetate and the extracts washed twice with water, once with sodium bicarbonate solution, once more with water, then dried over sodium sulfate. After evaporation of the extract, the solid residue is crystallized from 15 ml. acetonitrile.

I claim:
1. A method of preparing compounds selected from the group consisting of

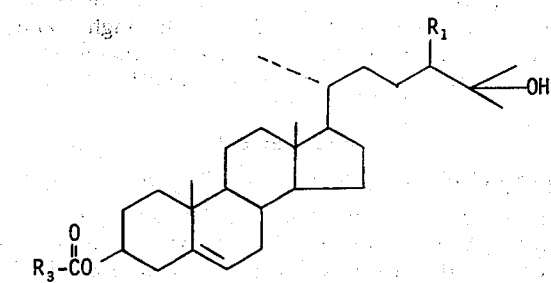

wherein R$^1$ is hydrogen or methyl and R$^3$ is alkyl of one to five carbon atoms, inclusive, which comprises
  a. reacting an aryl Wittig reagent with

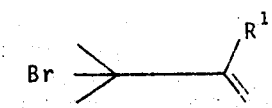

wherein R$^1$ is hydrogen or methyl, to form the phosphonium salt

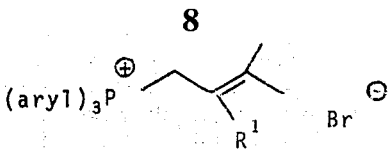

wherein R$^1$ is hydrogen or methyl
  b. converting the phosphonium salt to the ylide

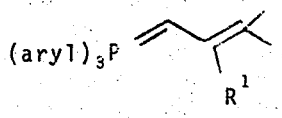

wherein R$^1$ is hydrogen or methyl
  c. condensing the ylide of Step b with 3α,5α-cyclo-6β-alkoxybisnorcholanaldehyde

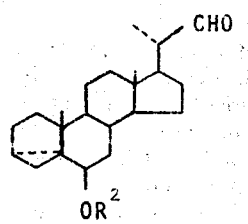

wherein R$^2$ is alkyl of one to six carbon atoms, inclusive, to form the compound

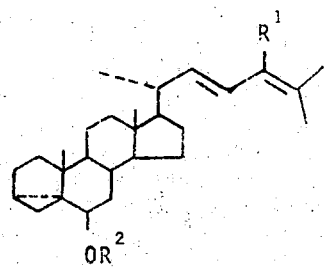

wherein R$^1$ and R$^2$ are as defined above;
  d. selectively epoxidizing the compound formed in Step c with peralkanoic acid having alkyl of one to four carbon atoms, inclusive, or peraroic acid, aryl having six to 10 carbon atoms, inclusive, to form the compound

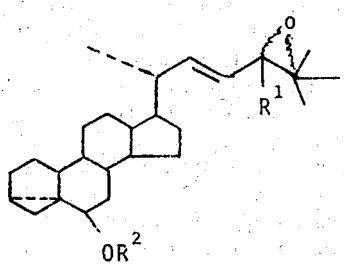

R$^1$ and R$^2$ as defined above;
  e. catalytically hydrogenating the unsaturated epoxide formed in Step d with a noble metal catalyst to form

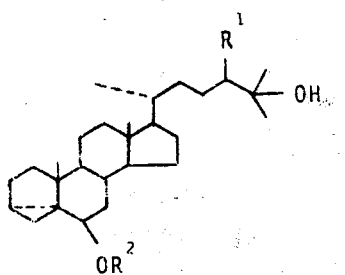

wherein R¹ and R² are as defined above, and f. reversing the i-ether of Step *e* with alkanoic acid, said alkyl having one to five carbon atoms, inclusive to form

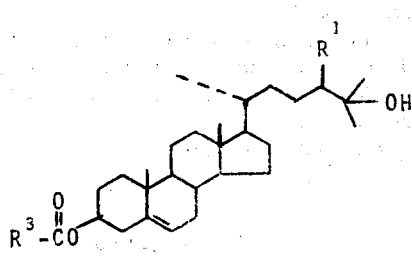

wherein R¹ is as defined above, and R³ is alkyl of one to five carbon atoms, inclusive.

2. A process in accordance with claim 1 wherein an inert organic solvent is present in the reaction medium of Steps *a*, *b*, *c*, *d*, and *e*.

3. A process for preparing compounds of the group

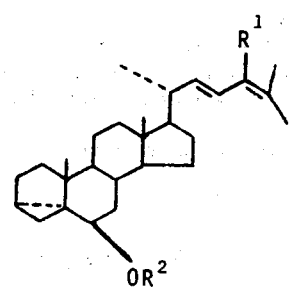

wherein R¹ is hydrogen or methyl and R² is alkyl of one to six carbon atoms, inclusive, which comprises condensing

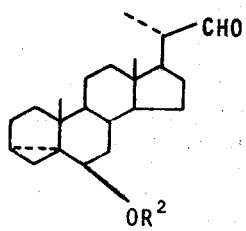

wherein R² is alkyl of one to six carbon atoms, inclusive, with

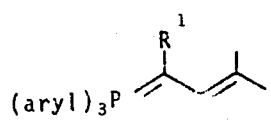

wherein R¹ is hydrogen or methyl in an alkane of five to eight carbon atoms, inclusive.

4. A process in accordance with claim 3 wherein the alkane is n-hexane.

5. A process for preparing compounds of the group

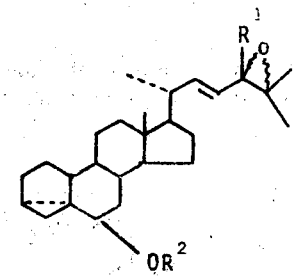

wherein R¹ is hydrogen or methyl and R² is alkyl of one to six carbon atoms, inclusive, which comprises selectively epoxidizing

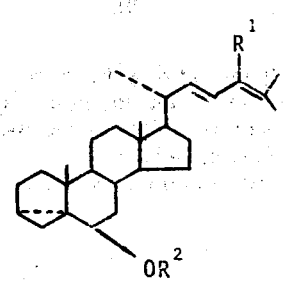

wherein R¹ and R² are as defined above with a peralkanoic acid, alkyl having one to four carbon atoms or a peraroic acid, said aryl having six to ten carbon atoms, inclusive.

6. A process in accordance with claim 5 wherein the peracid is peracetic acid or m-chloroperbenzoic acid.

7. A process in accordance with claim 6 wherein the peracid is peracetic acid.

8. A process for preparing compounds selected from the group

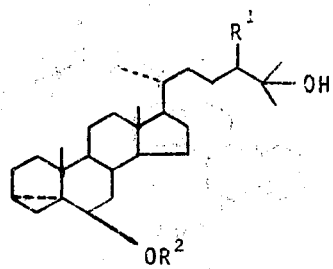

wherein R¹ is hydrogen or methyl and R² is alkyl of one to six carbon atoms, inclusive, which comprises a. condensing

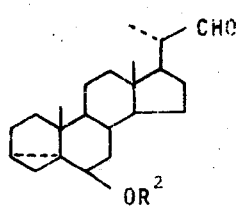

with an ylide

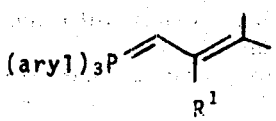

wherein R¹ is hydrogen or methyl and R² is alkyl of one to six carbon atoms, inclusive, to form

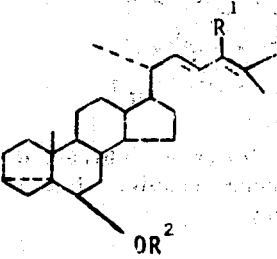

b. selectively epoxidizing the diene of Step a with a peracid selected from the group consisting of per alkanoic acids with alkyl having one to four carbon atoms, inclusive, and a peraroic acid with aryl having six to 10 carbon atoms, inclusive, to form

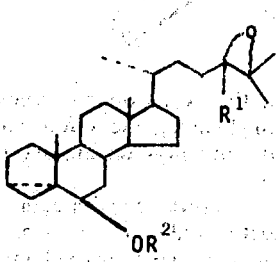

c. hydrogenating the epoxide of Step b in the presence of a noble metal catalyst to form

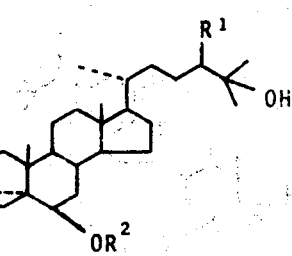

wherein R¹ and R² are as defined above.

9. A process in accordance with claim 8 wherein the per acid is acetic acid and the noble metal is platinum.

10. Compounds of the group

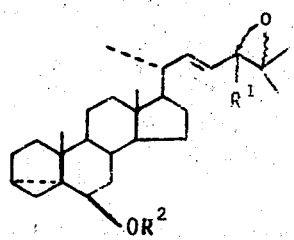

wherein R¹ is hydrogen or methyl and R² is alkyl of one to six carbon atoms, inclusive.

11. Compounds in accordance with claim 10 wherein R¹ is hydrogen.

12. compounds in accordance with claim 11 wherein R² is alkyl of one to three carbon atoms, inclusive.

13. Compounds in accordance with claim 10 wherein R² is methyl.

14. Compounds of the group

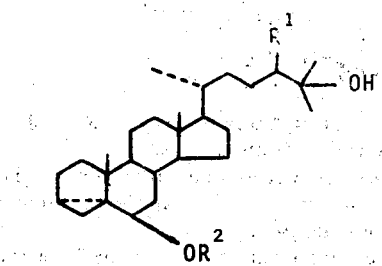

wherein R¹ is methyl and R² is alkyl of one to six carbon atoms, inclusive.

15. Compounds in accordance with claim 14 wherein R² is alkyl of one to three carbo atoms, inclusive.

16. Compounds in accordance with claim 14 wherein R² is methyl.

17. A compound of the formula

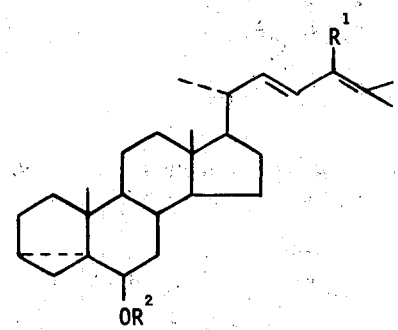

wherein R¹ is hydrogen or methyl and R² is alkyl of one to six carbon atoms, inclusive.

* * * * *

UNITED STATES PATENT AND TRADEMARK OFFICE
CERTIFICATE OF CORRECTION

PATENT NO. : 3,976,636
DATED : August 24, 1976
INVENTOR(S) : William G. Salmond

It is certified that error appears in the above—identified patent and that said Letters Patent is hereby corrected as shown below:

Column 2, line 42; change "groups" to --group--.

Column 5, line 58; change "now the" to --of the--.

Column 11, lines 32-34; change 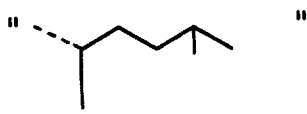 to 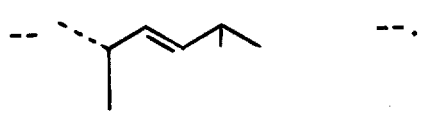 .

Column 12, line 37; change "carbo" to --carbon--.

Column 12, line 38; change "14" to --15--.

Signed and Sealed this

Twenty-ninth Day of July 1980

[SEAL]

Attest:

SIDNEY A. DIAMOND

Attesting Officer

Commissioner of Patents and Trademarks